United States Patent
Hendrickson et al.

(10) Patent No.: US 8,741,337 B2
(45) Date of Patent: *Jun. 3, 2014

(54) ENCAPSULATION OF OXIDATIVELY UNSTABLE COMPOUNDS

(75) Inventors: William A. Hendrickson, Woodbury, MN (US); John M. Finney, Eden Prairie, MN (US); Olaf C. Moberg, New Brighton, MN (US); Christopher J. Rueb, St. Paul, MN (US); Robert G. Bowman, Woodbury, MN (US); Chetan S. Rao, Austin, MN (US); Nita M. Bentley, Austin, MN (US)

(73) Assignee: Aveka, Inc., Woodbury, MN (US)

( * ) Notice: Subject to any disclaimer, the term of this patent is extended or adjusted under 35 U.S.C. 154(b) by 200 days.

This patent is subject to a terminal disclaimer.

(21) Appl. No.: 12/811,479

(22) PCT Filed: Jan. 2, 2009

(86) PCT No.: PCT/US2009/030054
§ 371 (c)(1),
(2), (4) Date: Nov. 12, 2010

(87) PCT Pub. No.: WO2009/089117
PCT Pub. Date: Jul. 16, 2009

(65) Prior Publication Data
US 2011/0052680 A1 Mar. 3, 2011

Related U.S. Application Data

(60) Provisional application No. 61/010,073, filed on Jan. 4, 2008.

(51) Int. Cl.
*A61K 9/127* (2006.01)
*A61J 3/07* (2006.01)
*A23L 2/00* (2006.01)
*A23L 1/221* (2006.01)

(52) U.S. Cl.
USPC .......... 424/450; 424/451; 106/243; 106/503; 264/4; 426/599; 426/650

(58) Field of Classification Search
None
See application file for complete search history.

(56) References Cited

U.S. PATENT DOCUMENTS

| | | | |
|---|---|---|---|
| 2,809,895 A | 10/1957 | Swisher |
| 4,765,996 A | 8/1988 | Misaki et al. |
| 5,260,279 A | 11/1993 | Greenberg |
| 5,418,010 A | 5/1995 | Janda et al. |
| 5,620,873 A | 4/1997 | Ohkuma et al. |
| 5,780,056 A | 7/1998 | Akamatsu et al. |
| 5,968,365 A | 10/1999 | Laurenzo et al. |
| 6,087,353 A | 7/2000 | Stewart et al. |
| 6,113,972 A | 9/2000 | Corliss et al. |
| 6,146,645 A | 11/2000 | Deckers et al. |
| 6,183,762 B1 | 2/2001 | Deckers et al. |
| 6,210,742 B1 | 4/2001 | Deckers et al. |
| 6,248,363 B1 | 6/2001 | Patel et al. |
| 6,281,375 B1 | 8/2001 | Kodali et al. |
| 6,372,234 B1 | 4/2002 | Deckers et al. |
| 6,582,710 B2 | 6/2003 | Deckers et al. |
| 6,596,287 B2 | 7/2003 | Deckers et al. |
| 6,599,513 B2 | 7/2003 | Deckers et al. |
| 6,638,547 B2 | 10/2003 | Perlman et al. |
| 6,638,557 B2 | 10/2003 | Qi et al. |
| 6,761,914 B2 | 7/2004 | Deckers et al. |
| 6,818,296 B1 | 11/2004 | Garces Garces et al. |
| 6,858,666 B2 | 2/2005 | Hamer et al. |
| 6,924,363 B1 | 8/2005 | Moloney et al. |
| 6,969,530 B1 | 11/2005 | Curtis et al. |
| 6,979,467 B1 | 12/2005 | Garces Garces et al. |
| 7,126,042 B1 | 10/2006 | McCarthy |
| 7,144,595 B2 | 12/2006 | Perlman et al. |
| 7,179,480 B2 | 2/2007 | Klassen |
| 7,237,679 B1 | 7/2007 | Hendrickson et al. |
| 7,279,121 B2 | 10/2007 | Hayashi |
| 7,374,788 B2 | 5/2008 | Augustin et al. |
| 2002/0037303 A1 | 3/2002 | Deckers et al. |
| 2002/0048606 A1 | 4/2002 | Zawistowski |
| 2003/0180352 A1 | 9/2003 | Patel et al. |
| 2003/0193102 A1 | 10/2003 | Yan |
| 2004/0067260 A1 | 4/2004 | Milley et al. |
| 2004/0156887 A1 | 8/2004 | Auriou |
| 2005/0032757 A1 | 2/2005 | Cho |
| 2005/0106157 A1 | 5/2005 | Deckers et al. |
| 2005/0181019 A1 | 8/2005 | Palmer et al. |
| 2005/0214346 A1 | 9/2005 | Bringe et al. |
| 2005/0249952 A1 | 11/2005 | Vasishtha et al. |

(Continued)

FOREIGN PATENT DOCUMENTS

JP 2002-101820 4/2002

OTHER PUBLICATIONS

Desai KGH and Park HJ, Recent Developments in Microencapsulation of Food Ingredients, Drying Technology, 23(7), pp. 1361-1394 (2005).
Ostlund R.E. Jr.et al., "Phytosterols that are naturally present in commercial corn oil significantly reduce cholesterol absorption in humans", Am. J. Clin Nutr., vol. 75, pp. 1000-1004 (2002).
Venkat, C., "Omega-3 Fatty Acids", 10 pages (2005), downloaded on Jun. 27, 2012 from: http://clltopics.org/Phyto/Omega3.htm.
Lawson, Harry, "Food Oils and Fats, Technology, Utilization, and Nutrition", New York; Chapman & Hall, pp. 18-22 (1995).

(Continued)

*Primary Examiner* — Doug Schultz
(74) *Attorney, Agent, or Firm* — IPLM Group, P.A.

(57) ABSTRACT

An encapsulated material containing an oxidation-sensitive core is covered by at least a dried phospholipid layer, and contains at least one phytosterol in the core, the phospholipid layer or in a further layer or layers. By using microencapsulation, oxidatively unstable materials may be provided with a synthetic protective barrier and rendered less susceptible to oxidative degradation.

17 Claims, 2 Drawing Sheets

(56) References Cited

U.S. PATENT DOCUMENTS

| | | |
|---|---|---|
| 2006/0034937 A1 | 2/2006 | Patel |
| 2006/0233862 A1 | 10/2006 | Alander |
| 2006/0251790 A1 | 11/2006 | Perlman et al. |
| 2007/0077308 A1 | 4/2007 | Giner |
| 2007/0098854 A1 | 5/2007 | Van Lengerich et al. |
| 2007/0122397 A1 | 5/2007 | Sanguansri et al. |
| 2007/0196914 A1 | 8/2007 | Murray et al. |
| 2007/0212475 A1 | 9/2007 | Augustin et al. |
| 2007/0218125 A1 | 9/2007 | Head et al. |
| 2008/0026108 A1 | 1/2008 | Subramanian et al. |
| 2011/0059164 A1* | 3/2011 | Hendrickson et al. .......... 424/451 |

OTHER PUBLICATIONS

Hilder, Martin H., "Oil Storage, Transport, and Handling", Chapter 7 of Gunstone et al., "Lipid Technologies and Applications" (New York; Marcel Dekker, Inc.), pp. 169-199 (1997).

Tzen, J. T. C. and Huang, A. H. C., "Surface Structure and Properties of Plant Seed Oil Bodies", J. Cell Bio, 117; 327-335 (1992).

Millichip, M., Tatham, A. S., Jackson, F., Griffiths, G., Shewry, P. R., and Stobart, A. K., "Purification and Characterization of Oil-Bodies (oleosomes) and Oil-Body Boundary Proteins (oleosins) for the Developing Cotyledons of Sunflower (*Helianthus annus* L.)", Biochem. J., 314; 333-337 (1996).

Huang, A. H. C., "Oleosins and Oil Bodies in Seed and Other Organs", Plant Physiol., 110; 1055-1061 (1996).

Ting, J. T. L., Balsamo, R. A., Ratnayake, C., Huang, A. H. C., "Oleosin of Plant Seed Oil Bodies is Correctly Targeted to the Lipid Bodies in Transformed Yeast", J. Bio. Chem. 272; 3699-3706 (1997).

Leon Prosky, J. of AOAC Int'l. 82:223-35(1999).

Wang, L., "Properties of Soybean Oil Bodies and Oleosin Proteins as Edible Films and Coatings, Ph.D. Thesis", Purdue University, UMI Microfilm 3150845 (May 2004).

Augustin, M.A. et al., "Maillard Reaction Products as Encapsulants for Fish Oil Powders", Journal of Food Science, vol. 71, No. 2, pp. E25-E32 (Mar. 2006).

Tzen, Jason T.C. et al., "Coexistence of Both Oleosin Isoforms on the Surface of Seed Oil Bodies and Their Individual Stabilization to the Organelles", The Journal of BioChemistry, vol. 123, No. 2, pp. 318-323 (Feb. 1998).

GAT Microencapsulation AG, "GAT Food Essentials_smart natural food ingredients", Product Information Brochure (2007).

Hou, R.C.W. et al., "Increase of Viability of Entrapped Cells of *Lactobacillus delbrueckii* ssp. *bulgaricus* in Artificial Sesame Oil Emulsions", Journal of Dairy Science, vol. 86, No. 2, pp. 424-428 (2003).

"Life's DHA™", Product & Services Information Sheet, Martek Biosciences Corporation, 1 page, downloaded on Jun. 10, 2008 from the following website: http://commercial.martek.com/animalnutrition/dhagoldproducts/.

"KOBO Glycospheres and Corneosperes", Product Information Sheets, 2 pages, downloaded on Jun. 24, 2008 from the following website: http://www.koboproductsinc.com/Glycospheres.html.

"Kuhs Kosmetik", cosmetic concepts Products Probiol®, Product Information Sheet, 1 page, downloaded on Jun. 24, 2008 from the following website: http://www.kuhs.com/en/products_probiol.html.

Sanguansri, L. and Augustin, M.A., "Getting Long Chain Omega-3s Into the Food Supply: a Technical Opportunity for the Food Industry", Presentation at the 40th Anniversary AIFST Convention 2007, Melbourne Convention Centre, Melbourne, Australia (Jun. 24-27, 2007).

"PROBIOL®—Vitamins, PROBIOL®—Lipids, PROBIOL®—Liposomes", product information sheets, 6 pgs. May 2006.

* cited by examiner

ENCAPSULATION OF OXIDATIVELY UNSTABLE COMPOUNDS

CROSS REFERENCE TO RELATED APPLICATIONS

This application is a U.S. national stage entry under 35 U.S.C. §371 of International Application No. PCT/US2009/030054 filed Jan. 2, 2009 and published as WO 2009/089117 A1, which in turn claims priority from U.S. Provisional Application Ser. No. 61/010,073 filed Jan. 4, 2008.

FIELD

This invention relates to encapsulation of materials that are sensitive to oxidation.

BACKGROUND

In the past thirty years much new information on the benefits of a healthy diet has emerged. In addition to the traditional food pyramid, vitamins and minerals, a healthy diet may include components such as soluble and insoluble fiber for promoting gastrointestinal health, phytosterols for lowering cholesterol levels and promoting heart health, antioxidants for discouraging cancer and other inflammatory diseases, and omega-3 and omega-6 polyunsaturated fatty acids (PUFAs) for promoting heart and brain health. There has been considerable commercial interest in providing deliverable forms of such components even though in many cases the component may be oxidatively unstable. For example, companies which have introduced or announced PUFA-containing products or materials include BASF SE, Blue Pacific Flavors, GAT Food Essentials GmbH, Kerry Group PLC, Martek Biosciences Corp. and Ocean Nutrition Canada. Some of these products or materials are said to employ prilling, spray drying or encapsulation to limit premature PUFA oxidation.

The ability to store refined or extracted triacylglycerols (TAGs), antioxidants or natural colors such as anthocyanins in a dried powder form is one of the biggest challenges for food processors, see e.g., Lawson, Harry, *Food Oils and Fats, Technology, Utilization, and Nutrition*, New York; Chapman & Hall, pp 18-22 (1995) and Gunstone, Frank D. and Padley, Fred B., *Lipid Technologies and Applications*, New York; Marcel Dekker, Inc., pp 169-199 (1997).

There is at present an ongoing and unmet need for improved methods and systems for packaging, storing or delivering PUFAs, TAGs, antioxidants, natural colors and other oxidatively unstable materials.

SUMMARY OF THE INVENTION

By using microencapsulation to protect oxidatively unstable cores, oxidatively unstable materials may be provided with a synthetic, oxygen-resistant protective barrier and rendered less susceptible to oxidative degradation. An oxidation-susceptible material (in the form, for example of a core per se or an already-encapsulated core) is encapsulated or further encapsulated in a dried synthetic phospholipid-containing layer, and a phytosterol is included in one or both of the core or a surrounding layer, to provide an encapsulated material whose core has improved oxidation resistance. This encapsulated material may be provided with additional functional or protective ingredients or shell layers to form a complex multi-component or multi-layered protective system for oxidation-sensitive cores. One such additional layer may be a fiber/carbohydrate/protein or FPC layer made using a fiber-, carbohydrate or protein-containing film-forming material. Another such additional layer may be a hydrocolloid or HC layer made using a natural or chemically-modified hydrocolloid material, e.g., an alginate.

The resulting microcapsules include an oxidatively unstable core, dried phospholipid shell or PS, and phytosterol. The microcapsules may be further modified, e.g., by adding the materials for an FCP layer or HC layer (as components of the PS or as separate layers), antioxidants, chelating agents, deodorized oils, oleosins or other dissolved, suspended or dispersed ingredients to one or more of the core or shell layer(s) to provide unique structures for stable oil or powder delivery in pharmaceutical, dietary, cosmetic, agricultural and other commercial uses. The disclosed encapsulated materials and methods are especially useful for imparting improved oxidation protection to difficult to protect core materials such as unsaturated and polyunsaturated oils and acids.

The present invention accordingly provides, in one aspect, an encapsulated material comprising an oxidation-sensitive core covered by at least one shell comprising a dried phospholipid layer, and having at least one phytosterol in the core or in a shell surrounding the core. The invention provides, in another aspect, a method for protecting an oxidatively unstable material, which method comprises providing or forming a particle or droplet of the oxidatively unstable material and forming a dried phospholipid layer surrounding the particle or droplet, wherein the particle, droplet, or a layer surrounding the particle or droplet contains at least one phytosterol.

The disclosed encapsulated materials and methods may provide processed oils and other oxidatively unstable materials with enhanced oxidative stability and in an effectively dry powder form.

DETAILED DESCRIPTION

Figure 1:
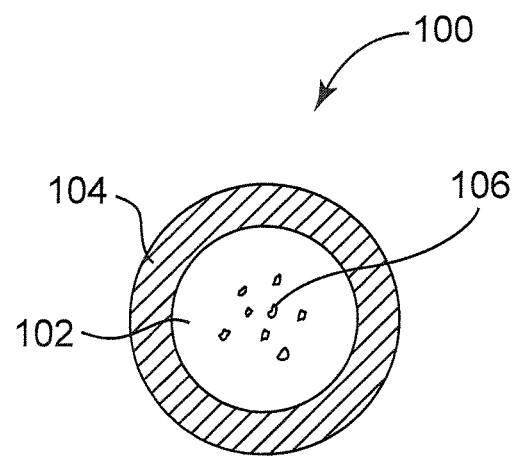
FIG. 1 through FIG. 4 are schematic cross-sectional views of various encapsulated materials.

Unless the context indicates otherwise the following terms shall have the following meaning and shall be applicable to the singular and plural:

The terms "a," "an," "the," "at least one," and "one or more" are used interchangeably. Thus a microcapsule that contains "a" shell may include "one or more" shells.

The term "deliverable" when used with respect to an encapsulated substance means that the substance is at least partially surrounded by an additional substance that imparts one or more altered properties to the encapsulated substance, e.g., altered transport, altered flowability, altered resistance to oxidation or moisture, altered abrasion resistance, or altered performance in a commercial application (e.g., a food application).

The term "dried" does not necessarily refer to a process of manufacture, but rather to the available water content in an article or component (e.g., a layer) thereof. The term "available water" does not include water of hydration.

The terms "encapsulated material" and "microcapsule" mean particles (often but not always spherical in shape, and often but not always having a diameter of about 10 nanometers to about 5 mm) which contain at least one liquid, gel or solid core surrounded by at least one continuous membrane or shell.

The term "ingestible" means capable of and safe for oral administration.

The term "microsphere" means a microcapsule material whose particles contain two or more cores distributed in and surrounded by at least one continuous membrane or shell.

The term "particulate" means a finely divided dry powder material.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The recitation of a numerical range using endpoints includes all numbers subsumed within that range (e.g., 1 to 5 includes 1, 1.5, 2, 2.75, 3, 3.80, 4, 5, etc.). The recitation of sets of upper and lower endpoints (e.g., at least 1, at least 2, at least 3, and less than 10, less than 5 and less than 4) includes all ranges that may be formed from such endpoints (e.g., 1 to 10, 1 to 5, 2 to 10, 2 to 5, etc.).

The disclosed encapsulated materials include at least an oxidation sensitive core and at least one shell layer containing a dried phospholipid layer over the core. Preferably the phospholipid layer is immediately adjacent the core layer, but intermediate or additional shells may surround the core, the phospholipid layer, or both the core and phospholipid layer. For example, the above-mentioned HC layer may facilitate upper gastrointestinal (UGI) tract bypass when the disclosed encapsulated materials are orally administered to mammalian subjects. A particularly useful layer, especially over the phospholipid layer, is the above-mentioned FPC layer. Exemplary FPC layers may be formed from at least one of dietary fiber (e.g., food grade fiber), a simple carbohydrate (e.g., a monosaccharide or disaccharide such as a sugar), or a protein, and may also include at least one antioxidant. If the encapsulated material is not required to be ingestible, then the outer and if desired inner layers may be ingestible or not as desired, whereas for ingestible encapsulated materials at least the outermost layer is ingestible.

The various additional layer ingredients discussed above may also or instead be incorporated into the phospholipid layer. In some embodiments ingredients capable of forming one and optionally several layers are combined into the continuous phase of an emulsion containing droplets or particles of the core material. The emulsion may be processed (e.g., spray dried) to convert the emulsion into microcapsules having at least one dried shell layer. The various additional layer ingredients may arrange themselves into separate layers around the core droplets or particles (for example due to reasons such as stereochemistry, surface energy, oleophilicity, oleophobicity, hydrophilicity or hydrophobicity), or may form a matrix of ingredients from the continuous phase in a single shell layer surrounding the core droplets or particles.

The resulting encapsulated materials have a locked-in protective structure in the form of one or more shell layers surrounding an oxidatively-sensitive core, and may provide better protection against oxidation than that provided by an undried emulsion. The encapsulated materials may also employ a multi-tiered defensive approach involving oxygen barriers, lipophilic antioxidants and hydrophilic antioxidants.

FIG. 1 shows an exemplary deliverable encapsulated material 100 including an oxidatively unstable core 102 surrounded by an outer dried phospholipid layer 104. Layer 104 provides a protective and water vapor transmission-resistant shell over core 102. Core 102, phospholipid layer 104 or both contain at least one dissolved, suspended or dispersed phytosterol (not shown in FIG. 1). When present in core 102, a phytosterol may improve the oxidation resistance of oxidatively-sensitive materials present in core 102. When present in layer 104, a phytosterol may contribute to one or more properties such as oxidation stability (viz., limiting oxygen diffusion into the core), structural stability (viz., keeping the core inside the shell), or steric stability (viz., increasing the shell strength). Core 102 may optionally contain dispersed solid particles 106 which may alter the properties of core 102 or layer 104, or may provide other features to encapsulated material 100. Core 102 may be formed for example from liquid, gelled or solid particles of an oxidatively unstable material, e.g., a PUFA, TAG, antioxidant, natural color or mixture thereof. Phospholipid layer 104 may be formed for example by combining one or more phospholipids (e.g., lecithin) and other optional materials to provide a shell layer mixture. Particles 106 may be formed for example from solids including calcium salts, alginic acid and salts thereof including sodium or calcium alginate, chelating agents including citric acid, or antioxidants including ascorbic acid.

Figure 2:
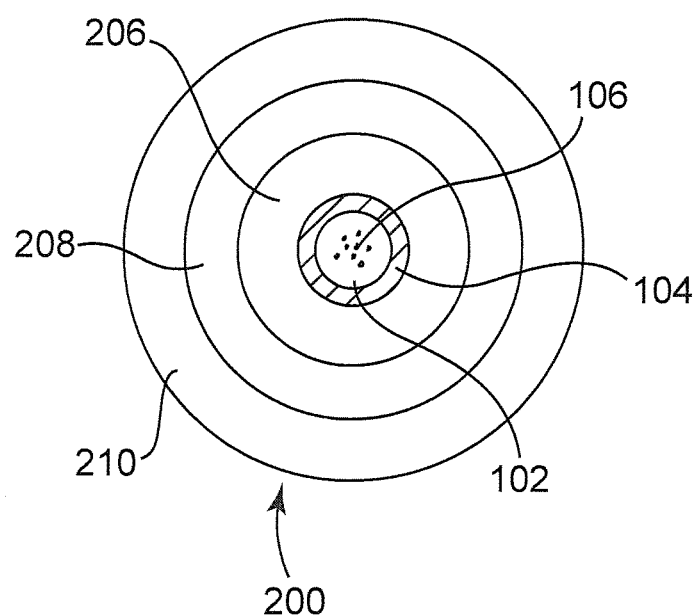

FIG. 2 shows another exemplary deliverable encapsulated material 200 including oxidatively unstable core 102 surrounded by dried phospholipid layer 104 and containing solid particles 106. Shell 104 is surrounded by an intermediate hydrocolloid shell 206 made for example from alginate, an intermediate fiber/carbohydrate shell 208 made for example from a mixture of maltodextrin, sucrose, trehalose and starch, and an outer protective layer 210 made for example from a mixture of lipid, fiber and protein. One or more of core 102 or layers or shells 104, 206 and 208 contain at least one phytosterol. The various layers shown in FIG. 2 are merely exemplary and may be rearranged, combined into fewer layers, augmented with additional layers or made from other ingredients or mixtures of ingredients. Doing so may facilitate formation of encapsulated materials which maintain, preserve or protect the core inside the encapsulated material and keep oxygen and if desired one or both of water or light away from the core.

Figure 3:
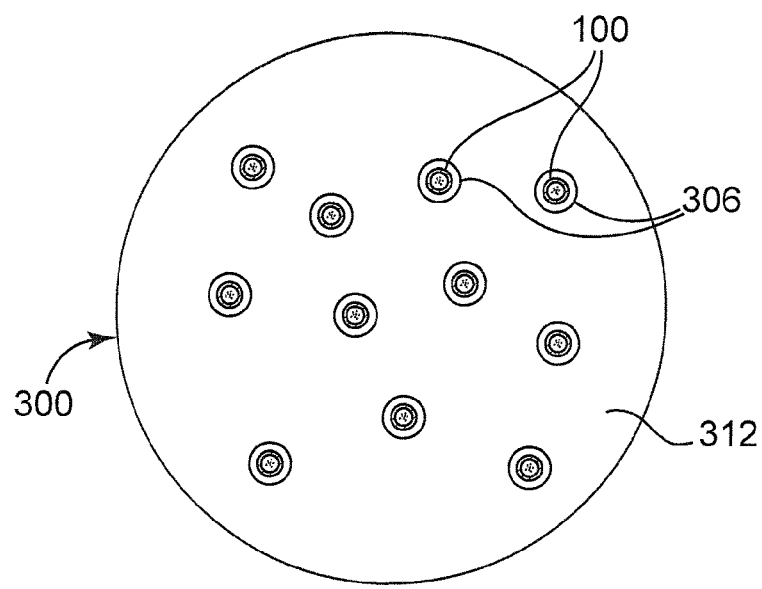

FIG. 3 shows another exemplary deliverable encapsulated material in the form of a microsphere 300 including a plurality of oxidatively unstable core particles 100 similar to those shown in FIG. 1 surrounded by intermediate hydrocolloid shells 306 made for example from alginate. The particles 100 and their shells 306 are dispersed in a protective matrix 312 made for example from a mixture of maltodextrin, sucrose, starch, ascorbic acid and oat fiber. One or more of the particles 100, shells 306 or matrix 312 contain at least one phytosterol.

Figure 4:
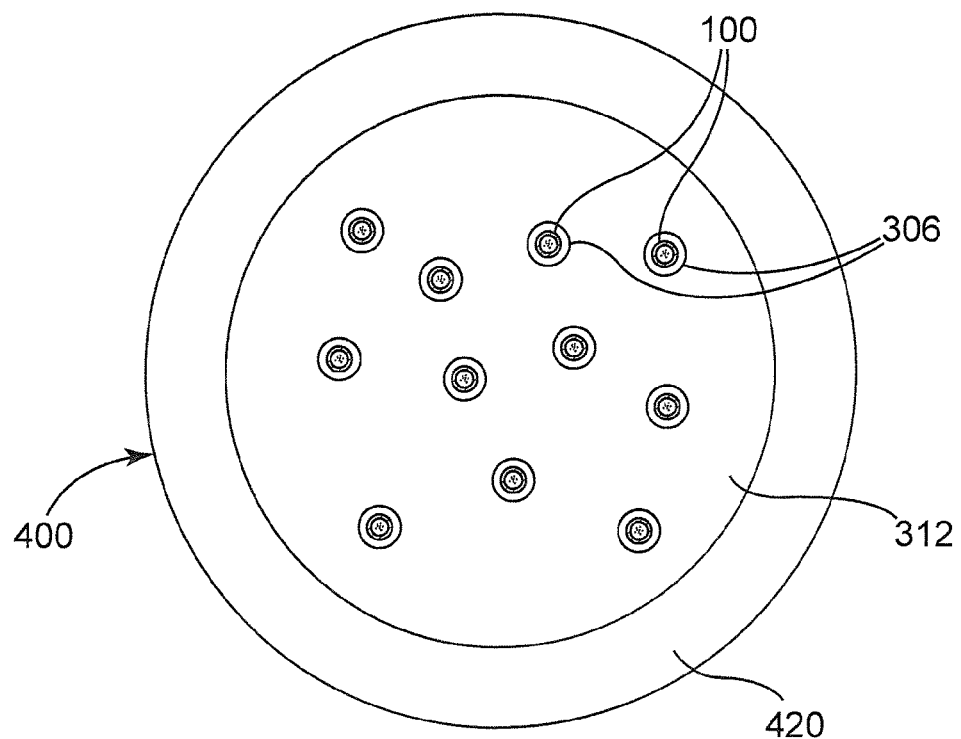

FIG. 4 shows another exemplary deliverable encapsulated material in the form of a microsphere 400 including a plurality of oxidatively unstable core particles 100 and surrounding intermediate hydrocolloid shells 306 dispersed in a protective matrix 312, and surrounded by a protective wax-containing shell 420. Shell 420 may include a variety of other ingredients, e.g., soluble fibers, lipid soluble materials including tocopherols, and dispersed water-soluble particulates including ascorbic acid and citric acid. One or more of the particles 100, shells 306, matrix 312 or shell 420 contain at least one phytosterol.

A variety of core substances may be used in the disclosed encapsulated materials. Exemplary oxidation-sensitive core substances include liquid or solid materials, e.g., acidulants, animal products, antioxidants, carotenoids, catalysts, drugs, dyes, enzymes, flavors, fragrances, lutein, lycopene, metal complexes, natural colors, nutraceuticals, pigments, polyphenolics, processed plant materials, metabiotics, probiotics, proteins, PUFAs, squalenes, sterols including phytosterols, tocopherol, tocotrienol, TAGs, vitamins, unsaturated organic compounds (e.g., unsaturated rubbers and unsaturated oils) and mixtures thereof. Antioxidants, PUFAs, sterols and TAGS are of particular interest. Antioxidants may, for example, suppress, reduce, intercept, or eliminate destructive radicals or chemical species that promote the formation of destructive radicals which would otherwise lead to more rapid oxidative degradation of the encapsulated material or components thereof. Exemplary antioxidants include menaquinone (vitamin $K_2$), plastoquinone, phylloquinone (vitamin $K_1$), retinol (vitamin A), tocopherols (e.g., α, β, γ and δ-tocotrienols, ubiquinol, and ubiquione (Coenzyme Q10)); and cyclic or polycyclic compounds including acetophenones, anthroquinones, benzoquiones, biflavonoids, catechol melanins, chromones, condensed tannins, coumarins, flavonoids, hydrolyzable tannins, hydroxycinnamic acids, hydroxybenzyl compounds, isoflavonoids, lignans, naphthoquinones, neolignans, phenolic acids, phenols (including bisphenols and other sterically hindered phenols, aminophenols and thiobisphenols), phenylacetic acids, phenylpropenes, stilbenes and xanthones. Additional cyclic or polycyclic antioxidant compounds include apigenin, auresin, aureusidin, Biochanin A, capsaicin, catechin, coniferyl alcohol, coniferyl aldehyde, cyanidin, daidzein, daphnetin, deiphinidin, emodin, epicatechin, eriodicytol, esculetin, ferulic acid, formononetin, gernistein, gingerol, 3-hydroxybenzoic acid, 4-hydroxybenzoic acid, 3-hydroxycoumarin, juglone, kaemferol, lunularic acid, luteolin, malvidin, mangiferin, 4-methylumbelliferone, mycertin, naringenin, pelargonidin, peonidin, petunidin, phloretin, p-hydroxyacetophenone, (+)-pinoresinol, procyanidin B-2, quercetin, resorcinol, rosmaric acid, salicylic acid, scopolein, sinapic acid, sinapoyl-(S)-maleate, sinapyl aldehyde, syrginyl alcohol, telligrandin umbelliferone and vanillin. Antioxidants may also be obtained from plant extracts, e.g., from blackberries, blueberries, black carrots, chokecherries, cranberries, black currants, elderberries, red grapes and their juice, hibiscus, oregano, purple sweet potato, red wine, rosemary, strawberries, tea (e.g., black, green or white tea), and from various plant ingredients as ellagic acid. Additional exemplary antioxidants include carotenoids including hydrocarbons such as hexahydrolycopene, lycopersene, phtyofluene, torulene and α-zeacarotene; alcohols such as alloxanthin, cynthiaxanthin, cryptomonaxanthin, crustaxanthin, gazaniaxanthin, loroxanthin, lycoxanthin, pectenoxanthin, rhodopin, rhodopinol and saproxanthin; glycosides such as oscillaxanthin and phleixanthophyll; ethers such as rhodovibrin and spheroidene; epoxides such as citroxanthin, diadinoxanthin, foliachrome, luteoxanthin, mutatoxanthin, neochrome, trollichrome, vaucheriaxanthin and zeaxanthin; aldehydes such as rhodopinal, torularhodinaldehyde and wamingone; ketones such as canthaxanthin, capsanthin, capsorubin, cryptocapsin, flexixanthin, hydroxyspheriodenone, okenone, pectenolone, phoeniconone, phoenicopterone, phoenicoxanthin, rubixanthone and siphonaxanthin; esters such as astacein, fucoxanthin, isofucoxanthin, physalien, siphonein and zeaxanthin dipalmitate; apo carotenoids such as β-apo-2'-cartoenal, apo-2-lycopenal, apo-6'-lycopenal, azafrinaldehyde, bixin, citranaxanthin, crocetin, crocetinsemialdehyde, crocin, hopkinsiaxanthin, methyl apo-6'-lycopenoate, paracentrone and sintaxanthin; nor and seco carotenoids such as actinioerythrin, β-carotene, peridinin, pyrrhoxanthininol, semi-α-carotenone, semi-β-carotenone and triphasiaxanthin; retro and retro apo carotenoids such as eschscholtzxanthin, eschscholtzxanthone, rhodoxanthin and tangeraxanthin; higher carotenoids such as decaprenoxanthin and nonaprenoxanthin; secondary aromatic amines; alkyl and arylthioethers; phosphates and phosphonites; zinc-thiocarbamates; benzofuranone lactone-based antioxidants; nickel quenchers; metal deactivators or complexing agents; and the like. Commercially available antioxidants include butylated hydroxyanisole (BHA), 2,6-di-t-butyl cresol (BHT), 2,2'-methylene bis(6-t-butyl-4-methyl phenol) (available as VULKANOX™ BKF from Bayer Inc., Canada), 2,2'-thio bis(6-t-butyl-4-methyl phenol), tert-butyl hydroquinone, di-tert-butyl hydroquinone, di-tert-amyl hydroquinone, methyl hydroquinone, p-methoxy phenol, tetrakis[methylene-3-(3',5'-di-tert-butyl-4'-hydroxyphenyl)propionate]methane, N-(2-aminoethyl)-3-[3,5-bis(tert-butyl)-4-hydroxyphenyl]propanamide, 5,7-di-tert-butyl-3-(3,4,-dimethylphenyl)-3H-benzofuran-2-one, dilauryl thiodipropionate, dimyristyl thiodipropionate, tris (nonylphenyl) phosphite, and the like, and mixtures thereof. The antioxidants 2,2'-methylene bis(6-t-butyl-4-methyl phenol) and N-(2-aminoethyl)-3-[3,5-bis(tert-butyl)-4-hydroxyphenyl]propanamide may be preferred for some applications, with the latter antioxidant being especially desirable because it includes a reactive amino group which may enable covalent incorporation into a suitably reactive core or shell.

Exemplary PUFAs include those found in fish and various grain products, e.g., fish oil, halibut, herring, mackerel, menhaden, salmon, algae, chia, flaxseed and soybeans. Exemplary sterols include cholesterol, phytosterols (e.g. campesterol, stigasterol, β-sitosterol, Δ5-avenosterol, Δ7-stigasterol, Δ7-avenosterol and brassicasterol), steroidal hormones such as testosterone, vitamins such as D vitamins, eicosanoids (e.g., hydroxyeicostetraones, prostacyclins, prostaglandins and thromboxanes, leukotrienes, lipoxins, resolvins, isoprostanes and jasmonates. Exemplary TAGs include those found in algae oil, almond oil, beef tallow, butterfat, canola oil, chia oil, cocoa butter, coconut oil, cod liver oil, corn oil, cottonseed oil, flaxseed oil, grape seed oil, lard, olive oil, palm oil, peanut oil, safflower oil, sesame oil, soybean oil, sunflower oil, and walnut oil.

The core may include additional ingredients having limited or no susceptibility to oxidation, e.g., caveolins, phospholipids, micelle stabilizers, and mixtures thereof. Exemplary phospholipids include those discussed below. Exemplary micelle stabilizers (some of which are phospholipids, discussed below) include cardolipin, digalactosyldiacylglycerols, monogalactosyldiacylglycerols, phosphatidylcholine, phosphatidylethanolamine, phosphatidylserine, phosphatidylinositol and sphingolipids and mixtures thereof. For core materials that normally are liquids at room temperature (25° C.), it will be desirable in some embodiments to gel the core. For example, core materials based on oils may be gelled as described in U.S. Pat. No. 6,858,666 B2 wherein an oxidation-sensitive oil or composition is heated in the presence of a suitable gelation agent to melt and dissolve the gelation agent in the continuous oil phase. The resultant solution may then be atomized and cooled to form particles. Exemplary gelled core particles may for example have particle diameters from about 0.1 to about 5,000 micrometers. The amount of gelation agent(s) may for example range from about 1 to about 90 wt. % of the core weight. Other additives including various salts, soluble or insoluble fibers, or additional oils may be added to the mixture. Additional exemplary gelled core particles based on PUFAs may be formed by combining a PUFA with a sterol, e.g., to form triglyceride-recrystallized phytosterols as in U.S. Pat. Nos. 6,638,547 B2 and 7,144,595 B2. Some antioxidants, e.g., Vitamin E, may also help convert a liquid core material to a gel.

The core may for example represent at least about 5 wt. %, at least about 20 wt. % or at least about 30 wt. % of the disclosed encapsulated materials. Desirably the core is greater than 30 wt. % of the encapsulated material, e.g., at least about 40 wt. % or at least about 50 wt. %.

The disclosed dried phospholipid layer may comprise, consist of or consist essentially of phospholipid or of phospholipid and phytosterol. The phospholipid may be chemically modified. A variety of phospholipids may be used to form the disclosed phospholipid layer. Exemplary phospholipids include natural or chemically modified phospholipids, e.g., alkylphosphocholines (viz., synthesized phospholipid-like molecules), cardiolipin, dipalmitoylphosphatidylcholine, glycerophospholipid, lecithin, phosphatidic acid, phosphatidylcholine, phosphatidylethanolamine, phosphatidylglycerol, phosphatidylinositol, phosphatidylinositol 3-phosphate, phosphatidylinositol (3,4)-bisphosphate, phosphatidylinositol (3,5)-biphosphate, phosphatidylinositol (3,4,5)-triphosphate, phosphatidylmyo-inositol mannosides, phosphatidylserine, sphingomyelin, sphingosyl phosphatide and mixtures thereof. An exemplary commercially available phospholipid is ULTRALEC F™ deoiled lecithin from Archer Daniels Midland Co. (Decatur, Ill.). In some embodiments the phospholipid layer or other layers may contain one or more antioxidants. Exemplary such antioxidants include those discussed above in connection with the core. Some antioxidants may be used as core stabilizers and as shell stabilizers. The phospholipid layer may be in direct contact with a surface of the core, or may be in direct contact with an intermediate protective layer located between a surface of the core and the phospholipid layer. The latter configuration may however have a reduced core content or core loading for a given particle size. The phospholipid layer may as discussed above be covered by one or more additional layers, for example a water-dispersible oxygen-barrier layer, hydrocolloid layer, lipophilic layer or any combination thereof.

The dried phospholipid layer may for example contain less than 8%, less than 6%, less than 5%, less than 4%, less than 3%, less than 2% or less than 1% of available water. The desired dryness level may be reached by removing water (e.g., if the phospholipid layer is formed using an aqueous carrier or solvent) or by adding water (e.g., if the phospholipid layer is formed using an organic carrier or solvent) after or during formation of the disclosed encapsulated material.

A variety of microencapsulating materials may be used in the disclosed encapsulated materials to form additional shell(s), sometimes also referred to as coatings or membranes, surrounding the core(s), or as additives in the phospholipid layer. Exemplary such materials may comprise, consist of or consist essentially of natural, semisynthetic (viz., chemically modified natural materials) or synthetic materials. Exemplary natural materials include gum arabic, agar agar, agarose, maltodextrins, alginic acid and salts thereof including sodium or calcium alginate, fats and fatty acids, cetyl alcohol, collagen, chitosan, lecithins, gelatin, albumin, shellac, polysaccharides including starch or dextran, polypeptides, protein hydrolyzates, sucrose and waxes. Oleosins as described in copending application Ser. No. 12/811,459, filed Nov. 23, 2010, may also be employed as additives in the phospholipid layer. Exemplary semisynthetic materials include chemically modified celluloses including cellulose esters and ethers (for example cellulose acetate, ethyl cellulose, hydroxypropyl cellulose, hydroxypropyl methyl cellulose and carboxymethyl cellulose) and chemically modified starches including starch ethers and esters (for example, CAPSUL™ modified starch from National Starch). Exemplary synthetic materials include polymers (for example, polyacrylates, polyamides, polyvinyl alcohol, polyvinyl pyrrolidone, polyureas and polyurethanes). Exemplary commercial microcapsule products (the shell materials for which are shown in parentheses) include Hallcrest Microcapsules (gelatin, gum arabic), Coletica THALASPHERES™ (maritime collagen), Lipotec MILLICAPSELN™ (alginic acid, agar agar), Induchem UNISPHERES™ (lactose, microcrystalline cellulose, hydroxypropylmethyl cellulose), Unicerin C30 (lactose, microcrystalline cellulose, hydroxypropylmethyl cellulose), Kobo GLYCOSPHERES™ (modified starch, fatty acid esters), SOFTSPHERES™ (modified agar agar) and Kuhs Probiol NANOSPHERES™.

A variety of phytosterols may be included in any or each of the core, phospholipid layer or other layers of the disclosed encapsulated materials. Exemplary phytosterols include campesterol, stigasterol, β-sitosterol, Δ5-avenosterol, Δ7-stigasterol, Δ7-avenosterol and brassicasterol. The phytosterol may for example represent about 0.01 to about 90, about 0.5 to about 80 or about 2 to about 60 wt. % of the encapsulated material.

A variety of natural or chemically modified fiber materials may be used to make FCP layers or as additives in the core, phospholipid layer or other layers. Fiber or "roughage" is a component of food that remains undigested as it passes through the gastrointestinal system, and which does not necessarily have a fibrous structure. The vast majority of dietary fiber consists of complex carbohydrates (e.g., polysaccharides) of plant origin, for example the cellulosic wall that surrounds plant cells. Fibers may be further classified into insoluble fibers such as the classic cellulosic materials, and soluble fibers such as water-soluble polysaccharides that are not digested by human or carnivore digestive systems. Both types of fiber bind considerable water and, thus, have a softening effect on the stool. Soluble fiber may, depending on the precise polysaccharides involved, also be metabolized or partially metabolized directly by bacteria in the colon, and may promote growth of beneficial bacteria. Both insoluble and soluble fibers tend to increase motility within the gastrointestinal tract thus speeding transit time of wastes and lowering the risk of acute and chronic medical problems. This generally has a positive effect as the beneficial bacteria may also tend to lubricate the stool and prevent the growth of other bacteria which may release toxins (see e.g., Leon Prosky, J. of AOAC Int'l. 82:223-35(1999)). Insoluble fibers may be obtained from a wide variety of sources. Exemplary insoluble fibers include almond fiber, cellulose, chia fiber, citrus fiber, coconut fiber, corn fiber, cottonseed fiber, flaxseed fiber, grape seed fiber, hemicelluloses, lignin, oat fiber, rice hulls, safflower fiber, sesame fiber, soybean fiber, sunflower fiber, and walnut fiber. Sources include whole grain foods, nuts and seeds, vegetables such as green beans, cauliflower, celery and zucchini, and the skins of some fruits (e.g. tomatoes). Soluble fibers may be obtained from a wide range of plant sources, including water-soluble plant pectins and pectic materials, galactomannans, arabanogalactans and water-soluble hemicellulose. Many plant "mucilages," gums, and soluble polysaccharides found in grains, seeds, or stems such as psyllium, guar, oat (beta glucans), astragalus (gum traganth), gum ghatti, gum karaya (Sterculia gum); and gum acacia also provide soluble fiber. Partially hydrolyzed guar gums may also provide soluble fiber, and may for example be prepared as described in U.S. Pat. No. 5,260,279. Algal polysaccharides such as agar or carrageenan (which as discussed below may also be used in an HC layer) behave as soluble fiber as do other digestible carbohydrates, such as maltodextrins or dextrins, produced by chemical or enzymatic digestion (e.g., partial hydrolysis) of starch, gums and other carbohydrate polymers. Dextrins or maltodextrins may for example be prepared by controlled hydrolysis of vegetable starches (e.g., potato or corn) as is described in U.S. Pat. No. 5,620,873 to Ohkuma et al. Soluble cellulosic ethers and other cellulose derivatives (e.g., carboxymethyl cellulose) behave as soluble fiber as do digestible carbohydrate polymers artificially prepared using bacterial enzymes. Storage carbohydrates such as lower molecular weight grades of inulin (see for example U.S. Pat. No. 5,968,365 to Laurenzo, et al.) are also important soluble fibers. Anionic chitosan derivatives, for example carboxylation and above all succinylation products of chitosan may also be used as soluble fibers. A number of companies now provide an entire range of soluble fiber materials. For example, TIC Gums of Belcamp, Md., Novartis Nutrition of Minneapolis, Minn. and Imperial Sensus of Sugar Land, Tex. provide food grade soluble fiber compounds. Additional soluble fibers are available in the United States as BENEFIBER™ from Novartis Nutrition of Minneapolis, Minn. or in other countries as SUN-FIBER™ from Taiyo of Japan. It is permissible and often advantageous to blend an assortment of different soluble fibers to create any particular fiber-water mixture. In fact the disclosed method may facilitate or dictate the selection of suitable fibers and their quantity or mode of delivery. Many of the various soluble fibers may have essentially identical properties when it comes to providing bulk and hydration to stools. However, selected soluble fibers may provide desirably altered solution clarity, lipid absorption, sugar absorption or other factors of interest. For example, among presently available soluble fibers, dextrins, inulins and partially hydrolyzed guar gum appear to provide aqueous solutions having the greatest degree of clarity. However, many dextrins and inulins contain a small amount of a metabolizable component and have a slight sweet taste. For some applications it will be advantageous to provide a portion of the soluble fiber in the form of hydrolyzed guar gum or some other flavorless and non-metabolizable compound, together with a second portion in the form of a metabolizable fiber such as an inulin. Even though some fibers may produce solutions having lower clarity, combinations with clear soluble fibers can yield a solution which is both high in fiber and clarity and low in sweetness or other taste. Other soluble fibers can be combined to realize the advantages of fiber mixtures.

A variety of natural or chemically modified carbohydrates may be used to make FCP layers or as additives in the core, phospholipid layer or other layers. Exemplary such carbohydrates include monosaccharides, disaccharides, trisaccharides and oligosaccharides such as dextrose, fructose, dextrose, galactose, glucose, lactose, mannose, ribose, sucrose, trehalose and xylose, as well as sugars contained in sources such as corn products, molasses, spent sulfite liquors, sugar beets, and their respective hydrolysates. Reducing sugars and non-reducing sugars may be employed. Reducing sugars may also be used to promote a Maillard reaction with proteins as discussed in more detail below.

A variety of natural or chemically modified proteins may be used to make FCP layers or as additives in the core, phospholipid layer or other layers. Exemplary such proteins include dairy proteins, e.g., casein, caseinate, milk protein concentrate (MPC), whey, whey protein concentrate (WPC) and whey protein isolate (WPI); processed proteins, e.g., albumin, albumen, collagen, gelatins (e.g., beef, fish or pork gelatin), soy protein concentrate (SPC) and wheat gluten; vegetarian proteins from nuts (e.g., almonds, beechnuts, brazil nuts, chestnuts, hazelnuts or walnuts) or from seeds. (e.g., amaranth, barley, beans, buckwheat, canola, chia, corn, flax, hemp, millet, oats, peanuts, peas, pumpkins, quinoa, rice, rye, sorghum, soybeans, sunflowers, wheat and wild rice; miscellaneous protein sources, e.g., algae, eggs and yeast; and animal protein sources, e.g., meat or blood portions of beef, buffalo, cephalopods, chicken, deer, ducks, eel, elk, emu, fish, geese, goat, ostrich, pork, rabbits, rodentia, sheep, shellfish, turkeys, water buffalo and yaks.

A variety of natural or chemically modified hydrocolloids may be used to make hydrocolloid shell (HCS) layers or as additives in the core, phospholipid layer or other layers. Exemplary hydrocolloids include alginates and other algal polysaccharides such as agar; carrageenans; gelatins; hyaluronates; modified starches; pectins; sulfated dextrans; xanthan gums; cellulose derivatives such as carboxymethyl cellulose, oxidized cellulose and microcrystalline cellulose; and mixtures thereof. Alginic acid, its salts and complete and partial neutralization products thereof may also be employed. Alginic acid is a mixture of carboxyl-containing polysaccharides with an idealized monomeric unit, and a weight average molecular weight of about 18,000 to about 120,000. Exemplary salts of alginic acid and complete and partial neutralization products thereof include alkali metal salts such as sodium alginate ("algin"), and ammonium and alkaline earth metal salts. Mixed alginates, for example sodium/magnesium or sodium/calcium alginates, may also be employed. Hydrocolloids may also be crosslinked, as discussed in more detail below.

The disclosed encapsulated materials may contain a variety of adjuvants, including chelating agents, surfactants, UV absorbers and other ingredients or additives that will be familiar to persons having ordinary skill in the microencapsulation art. Exemplary chelating agents include citric acid and ethylenediaminetetraacetic acid (EDTA). Exemplary surfactants include anionic, nonionic, cationic and amphoteric (zwitterionic) surfactants. Exemplary anionic surfactants include soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monolyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, protein fatty acid condensates (e.g., wheat-based vegetable products) and alkyl (ether) phosphates. Exemplary nonionic surfactants include fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (e.g., wheat-based vegetable products), polyol fatty acid esters, sugar esters, sorbitan esters, polysorbates and amine oxides. Cationic or nonionic surfactants containing polyglycol ether chains may have a conventional homolog distribution, but preferably have a narrow-range homolog distribution. Exemplary cationic surfactants include quaternary ammonium compounds, for example dimethyl distearyl ammonium chloride, and esterquats, more particularly quaternized fatty acid trialkanolamine ester salts. Exemplary amphoteric or zwitterionic surfactants include alkylbetaines, alkylamidobetaines, aminopropionates, aminoglycinates, imidazolinium betaines and sulfobetaines. Further details concerning these and other exemplary surfactants may be found for example in J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217.

UV absorbers act as stabilizers to protect the microcapsule by absorbing radiation in the range of about 270-500 nanometers and subsequently releasing the energy into the environment through non-destructive means. Exemplary UV absorbers include hindered amine light stabilizers (HALE), cinnamate esters, hydroxybenzophenones, benzotriazoles, substituted acrylates, salicylates, oxanilides, hydroxyphenyltriazines, nanoparticle titania, nanoparticle zinc oxide, and the like.

The disclosed encapsulated materials may also include absorbents, dehydrators, flow aids and other agents that may assist in pouring, storing or dispensing the encapsulated materials or in mixing them with other materials. The agent may in some embodiments form a coating over an outer layer, in effect representing an additional shell, and may in other embodiments be an additive included in an outer layer. The agent may change the surface energy of the encapsulated material, absorb excess oil, or serve other functions. Exemplary such agents include inorganic or organic materials such as activated carbon, alumina, aluminum phosphates, aluminium silicates, bentonite, bone phosphate, calcium aluminosilicate, calcium carbonate, calcium ferrocyanide, calcium silicate, magnesium oxides, magnesium silicates, magnesium trisilicate, oat or other fibers, Polydimethylsiloxane, potassium aluminium silicate, potassium ferrocyanide, powdered phytosterols, silicas (e.g., fumed or precipitated silicas), sodium aluminosilicate, sodium bicarbonate, silicon dioxide, sodium ferrocyanide, sodium silicate, stearic acid, talc, sodium phosphate, tricalcium phosphate, zeolites, and mixtures thereof. The agent may for example represent about 0.5 to about 5 wt. % of the encapsulated material.

The disclosed encapsulated materials may be prepared using a variety of encapsulation methods. For example, a solid particle of the core material may be fanned and a phospholipid layer may be deposited and dried on the solid particle while the particle is suspended or dispersed or in a trajectory, and with one or both of the core material or phospholipid layer containing a phytosterol. A droplet of the core material may instead be suspended or dispersed in a fluid environment containing a phospholipid composition, and with one or both of the core material or phospholipid composition containing a phytosterol. A droplet of the core material may also be spray dried or prilled in combination with materials forming the phospholipid layer, optionally together with additional materials which may become incorporated into the phospholipid layer or may form an additional layer or layers between the core and phospholipid layer or surrounding the phospholipid layer, and with the core material or layer material(s) containing a phytosterol. The materials forming the phospholipid layer may if desired be in fluid form at an elevated temperature (e.g., at above 30° C.) and in solid form when cooled to a lower temperature.

The various applied layers may be reacted with a variety of materials to alter some or all of the layer characteristics. This may be carried out using a variety of reaction schemes, materials and other measures. For example, a Maillard reaction between proteins and reducing sugars may be used to alter a layer containing protein or a layer containing a reducing sugar by exposing such layers to reducing sugar or protein, respectively, in the presence of sufficient heat to promote a browning reaction. Hydrocolloid (e.g., alginate layers) may be crosslinked, e.g., by inclusion of a suitable calcium salt source in the hydrocolloid layer, in an adjacent layer or in the core.

The following exemplary structures and methods may be used to form the disclosed encapsulated materials. An exemplary encapsulated material may for example be made using an oxidation-sensitive liquid core (e.g., a TAG or PUFA core) to which has been added a phytosterol and optionally an antioxidant (e.g., tocopherol, lycopene or tocotrienols), chelating agents, or dispersed calcium carbonate or calcium sulfate. The core may be formed by mixing or providing a portion of the active core ingredients at an appropriate temperature of, for example 70-80° C., then cooling and atomizing the mixture in a spray-drying or "prilling" column to form beads. The beads may be coated with a phospholipid shell or PS which may be made from a variety of materials (e.g., lecithin or other phospholipid-containing materials, and other optional ingredients). The thus-coated beads may be dried and a melt process may next be used to form one or more fiber/carbohydrate/protein shells with antioxidant properties over the PS, e.g. B.S. mixing the PS-coated cores into a portion of the melted fiber/carbohydrate/protein composition into which antioxidants have been dissolved, dispersed or suspended. This last step may be repeated several (e.g., one to four) times. HC shell (HCS) layers may be formed, for example from an aqueous sodium alginate hydrocolloid solution to which a variety of other materials may also be added. FCPS layers may be formed, for example by adding fibers such as insoluble fiber or carboxymethyl cellulose (CMC) fibers and optional additives to a solution containing water-soluble antioxidants and reducible sugars. The resulting mixture may be formed into encapsulated materials, e.g., by adding the PS-coated cores to the solution and spray drying to form FCP-coated particles. In a preferred process the resulting spray dried product is added to a melt for prilling or otherwise converted in order to form an outer lipophilic shell or LPS over an FCP-coated core. Separation of microcapsules by centrifugation or filtration and drying to a dry state may also or instead be used to form various layers.

Using these various general processes for manufacture, a variety of different materials, layers and constructions can be used to provide a variety of encapsulated materials. Set out below in Table 1 are several non-limiting exemplary structural components, ingredients and functions for use in such processes. The terms "AT" an "AO" in Table 1 respectively refer to an "active ingredient" and an "antioxidant", functions which in some cases may be performed by the same material. Typically an AI or AO will be carried and protected by the core, PS, HCS, FCPS or other layer until such time as the AI or AO may be delivered to an intended host or site for a subsequent designed use. Other abbreviations are identified in the footnotes to Table 1. To simplify the table appearance, the first row for each new structural component (e.g., Core, PS, etc.) includes the structural component label, and subsequent rows showing other materials for use in or as such structural component do not explicitly show the structural component label but are deemed to have been so labeled.

TABLE 1

| Structural Component | Ingredient | Function |
|---|---|---|
| Core | PUFA[1] | AI[2] |
|  | Vegetable Oil | AI or AO[3] |

TABLE 1-continued

| Structural Component | Ingredient | Function |
|---|---|---|
| | Lycopene | AI or AO |
| | Lutein | AI or AO |
| | Tocopherol | AI or AO |
| | Phytosterol | AI, organogellation agent or AO |
| | BHT[4] | AI or AO |
| | Calcium Compound | Crosslinking agent for HCS[5] |
| | Citric Acid | Metal chelating agent for prooxidants or AI |
| | EDTA[6] Salt | Metal chelating agent for prooxidants |
| Phospholipid Shell | Phospholipid | Liposome shell, core stabilizer and AO |
| | Phytosterol | Liposome shell stabilizer or AO |
| | Oleosin | Liposome shell stabilizer |
| Hydrocolloid Shell | Alginate | Shell Matrix, UGI[7] bypass and oxygen barrier |
| | CMC[8] | Shell, oxygen barrier |
| | Insoluble Fiber | Shell, oxygen barrier |
| | HPMC[9] | Shell, oxygen barrier |
| | Anthocyanin | AO |
| | BHT | AO |
| | Lutein | AO |
| | Lycopene | AO |
| | Tocopherol | AO |
| | Carbohydrate | AI |
| | Dextrose | Reducible sugar for Maillard reaction and carbohydrate |
| | Fructose | Reducible sugar for Maillard reaction and carbohydrate |
| | Lactose | Reducible sugar for Maillard reaction and carbohydrate |
| | Sucrose | Nonreducible sugar and carbohydrate |
| | Trehalose | Nonreducible sugar and carbohydrate |
| | Casein | Protein for Maillard reaction |
| | WPC[10] | Protein for Maillard reaction |
| | Phytosterol | AI, oxygen Barrier or AO |
| Fiber/Carbohydrate/ Protein Shell | Pectin | Soluble fiber for UGI bypass |
| | Insoluble Fiber | Oxygen barrier |
| | Alginate | Matrix, soluble fiber, oxygen barrier |
| | Starch | Matrix, soluble fiber, oxygen barrier |
| | Dextrose | Reducible sugar for Maillard reaction and carbohydrate |
| | Fructose | Reducible sugar for Maillard reaction and carbohydrate |
| | Lactose | Reducible sugar for Maillard reaction and carbohydrate |
| | Sucrose | Nonreducible sugar and carbohydrate |
| | Trehalose | Nonreducible sugar and carbohydrate |
| | Casein | Protein for Maillard reaction |
| | Gelatin | Matrix protein for Maillard reaction, oxygen barrier |
| | WPC | Protein for Maillard reaction |
| | Whey | Reducible sugar and protein for Maillard reaction |
| | Phytosterol | AI, oxygen barrier or AO |
| | Lycopene | AO |
| | Lutein | AO |
| | Tocopherol | AO |
| | BHT | AO |
| Lipophilic Shell | Hydrogenated Oil | Oxygen barrier, AO |
| | Phytosterol | AI, oxygen barrier or AO |

[1] PUFA is polyunsaturated fatty acid.
[2] AI is active ingredient.
[3] AO is antioxidant.
[4] BHT is 2,6-di-t-butyl cresol.
[5] HCS is hydrocolloid shell.
[6] EDTA is ethylenediaminetetraacetic acid.
[7] UGI is upper gastrointestinal tract.
[8] CMC is carboxymethylcellulose.
[9] HPMC is hydroxypropylmethylcellulose.
[10] WPC is whey protein concentrate.

For encapsulated materials having a core surrounded by a single PS layer, the core:shell weight ratio may for example range from about 10:1 to about 1:10, about 8:1 to about 1:1, or about 2:1 to about 2:3. For encapsulated materials having a core surrounded by four shell layers (e.g., a core having PS, HCS, FCPS and LPS layers), the core may for example represent about 5 to about 70, about 5 to about 60 or about 10 to about 40 wt. % of the total encapsulated material weight. Set out below in Table 2 are exemplary constructions showing core and layer amounts (expressed in parts by weight) for a variety of encapsulated materials containing PS-coated cores, alginate shells, FCP shells and lipophilic shells, together with the approximate core weight percent.

TABLE 2

| Layer | Example | | | | | |
|---|---|---|---|---|---|---|
| | A | B | C | D | E | F |
| Core | 80 | 80 | 80 | 80 | 80 | 80 |
| Oil Body Shell | 20 | 20 | 20 | 20 | 15 | 20 |
| Alginate Shell | 20 | 20 | 20 | 20 | 20 | 20 |
| Fiber/Carbohydrate/Protein Shell | 120 | 80 | 40 | 120 | 20 | 120 |
| Lipophilic Shell | 240 | 240 | 240 | 0 | 0 | 1400 |
| Percent Core | 16% | 18% | 20% | 33% | 60% | 5% |

The data in Table 2 show encapsulated materials with four shell layers containing about 5-60 wt. % core content. By varying the presence or absence of the various layer and their ingredients and relative amounts, encapsulated materials having a variety of properties can be formed. For example, if the lipophilic shell is eliminated and a fiber/carbohydrate/protein shell containing mainly a soluble fiber such as pectin or alginate is employed, a taste-masked encapsulated material with UGI bypass characteristics may be prepared. If a phytosterol-containing lipophilic shell is employed, a high temperature encapsulated material with an AO shell may be prepared for use in baked products and baking applications. Encapsulated materials whose cores or lipophilic shells contain organogels, and encapsulated materials with lipophilic shells containing hydrogenated oils crystallized in the beta form, may provide oxygen barrier or zero order (viz., concentration-independent) release characteristics.

Oxidative stability may be evaluated using a variety of tests. Simple but sensitive subjective tests such as olfactory tests or taste tests will suffice for many applications. A variety of objective may also be employed, including accelerated oxidative stress tests such as solid phase micro extraction (SPME) at an elevated temperature, e.g., 50° C. in an oxidizing atmosphere such as pure oxygen. Aging at 50° C. in pure oxygen represents a fairly severe test regime, and materials which provide low SPME values (or little change in the SPME value compared to the initial SPME value) when so aged may provide very good protection under less stringent (e.g., room temperature) storage conditions. The SPME value after 48 hours at 50° C. in pure oxygen may for example be less than 8,000, less than 5,000 or less than 4,000. The ratio of SPME after 48 hours at 50° C. to initial SPME may also be evaluated, and may for example be less than 8, less than 4, less than 2, less than 1.7 or less than 1.3. An SPME measurement for omega-3 oil may for example be carried out as follows:

SPME Oxidative Stress Test for Omega-3 Oil

Omega-3 oil samples are prepared by accurately weighing (to 0.1 mg) about 0.5 g of oil into a 5 cc serum bottle (Wheaton #223685), and adding a weighed portion of an internal standard made using 400 micrograms of dodecane per gram of mineral oil. Sufficient internal standard is normally employed to provide about 8 ppm dodecane in the sample. The bottle is sealed with a polytetrafluoroethylene-faced silicon septa and an aluminum crimp seal. For oxidative stress testing, two additional portions are sealed after flushing for 15 seconds with pure oxygen. These portions are held in an oven until evaluation (typically 24 hours or 48 hours at 50° C.). The bottle to be evaluated is thermostated for 30 minutes at 60° C. using a Pierce REACTITHERM™ heating bloc. The bottle headspace is then extracted for 30 minutes with a 50/30μ solid phase extraction fiber made from divinyl benzene/Carboxen™ fiber/polydimethylsiloxane/STABILFLEX™ fiber. The fiber is desorbed in the injection port of a gas chromatograph at 230° C. for 30 minutes. Typically, the next sample is thermostated at 60° C. during this 30 minute period. Chromatography is accomplished on a 20 meter RTX-CLP1 column with an ID of 0.18 mm and a 0.18 μm film thickness. The initial temperature is 45° C. for one minute, followed by heating at 3° C./minute to 60° C., then 2° C./minute to 140° C., and then finally 20° C./minute to 210° C. with a one minute hold at 210° C. to clear the column. The column is allowed to cool such that the total cycle time is 60 minutes. The flow rate is set to a constant velocity of 23 cm/second. A flame ionization detector (FID) set to maximum sensitivity is employed. Its response is calibrated using an SPME extraction of an approximate 25 milligram portion of a mineral oil standard containing 660 ppm 2-methyl 2-butene, 428 ppm ethyl benzene, 154 ppm hexane, 440 ppm 3-hexene-1-ol, 386 ppm 4-heptanal, 482 ppm 2,6-nonadienal and 404 ppm dodecane.

The disclosed encapsulated materials may be used in a variety of products and applications including foods, food additives, food supplements, prepared (e.g., baked, frozen or precooked) foods, nutraceuticals, medicines, catalysts, inks and coatings.

The invention is further described in the following Examples, in which all parts and percentages are by weight unless otherwise indicated.

Comparative Examples 1-3

Three samples of omega-3 oil (from Hormel Foods Corp.) containing 2,000 ppm tocopherols were evaluated for oxidative stability using SPME. An average SPME value of 28,663 was obtained after 48 hours at 50° C. (see Table 3).

Comparative Example 4

A starch solution was prepared by blending together 150 g of M200 maltodextrin (from Grain Processing Corp.), 30 g of CAPSUL™ modified starch (from National Starch) and 20 g of sucrose (from Rainbow Foods) and then adding the resulting blended powder mixture to 300 g of 80° C. deionized (DI) water. The solution was agitated as the temperature was increased to 85° C., then cooled in an ice bath before refrigerating overnight. The following day the solution was allowed to reach room temperature (about 25° C.) before adding an oil phase made from 50 g of omega-3 oil (from Hormel Foods Corp.) containing 2,000 ppm tocopherol. The oil was emulsified into the starch solution using a SILVERSON™ L2R high shear mixer (from Silverson Machines) operated at maximum speed for 3 minutes to create an oil-in-water emulsion. The emulsion was spray dried using a NIRO™ Mobile Minor lab dryer (from Niro Equipment Corp.) operated using an inlet temperature of 225° C. and an outlet temperature of 75° C. The product had an SPME value of 43,765 after 48 hours at 50° C. (see Table 3).

Comparative Example 5

An encapsulated product was prepared using the method of Comparative Example 4 but employing a starch solution made from 130 g of M100 maltodextrin (from Grain Processing Corp.), 30 g of CAPSUL modified starch and 40 g of sucrose (from Rainbow Foods) and then adding the resulting blended powder mixture to 300 g of 80° C. deionized (DI) water. The product had an SPME value of 39,985 after 48 hours at 50° C. (see Table 3).

Comparative Example 6

An encapsulated product was prepared using the method of Comparative Example 4 but employing a starch solution made from 110 g of M100 maltodextrin, 15 g of CAPSUL modified starch, 75 g of sucrose and 300 g of DI water, and an oil phase made from 50 g of omega-3 oil containing 2,000 ppm tocopherol. The resulting encapsulated product had an SPME value of 38,840 after 48 hours at 50° C. (see Table 3).

Example 1

A starch solution was prepared by blending together 600 g of M200 maltodextrin, 120 g of CAPSUL modified starch, 2.7 g of ascorbic acid and 80 g of sucrose and then adding the resulting blended powder mixture to 1,200 g of 80° C. DI water. The solution was agitated as the temperature was increased to 85° C., then cooled in an ice bath before refrigerating overnight. The following day 26.7 g of ULTRALEC F™ lecithin (from Archer Daniels Midland Co.) was added to 530.7 g of omega-3 oil (from Hormel Foods Corp.) containing 2,000 ppm tocopherol. The oil phase was heated to approximately 80° C. and allowed to cool, then emulsified into the starch solution using a SILVERSON L2R high shear mixer operated at maximum speed for 20 minutes followed by a single pass through a MICROFLUIDICS™ M110Y microfluidizer (from MFIC Corp.) operated at 103 MPa. The resulting emulsion was spray dried using a NIRO Mobile Minor lab dryer operated using an inlet temperature of 225° C. and an outlet temperature of 75° C. The total yield of product collected in bottles from the cyclone was 588 g. An additional 398 g of product was scraped from the spray drier after it cooled to room temperature. The product had an SPME value of 19,796 after 48 hours at 50° C. (see Table 3). This SPME value is substantially less than the average SPME value of 28,663 obtained for Comparative Examples 1, 2, and 3. The SPME value was also substantially less than the average SPME value of 38,265 obtained for the encapsulated product of Comparative Example 4, and substantially less than the SPME value of 51,200 obtained for the encapsulated product of Comparative Example 5. The Example 1 product accordingly provided improved oxidative stability over the Comparative Examples.

Example 2

An encapsulated product was prepared using the method of Example 1 but employing a starch solution containing 600 g of M200 maltodextrin, 120 g of CAPSUL modified starch, 4.0 g of ascorbic acid, 80 g of sucrose and 1,200 g of DI water, and an oil phase made from 40.0 g of lecithin and 796 g of omega-3 oil containing 2,000 ppm tocopherol. The total yield of product collected in bottles from the cyclone was 784 g. An additional 508 g of product was scraped from the dryer. The product had an SPME value of 10,355 after 48 hours at 50° C. (see Table 3), thus demonstrating improved oxidative stability over the Comparative Examples.

Example 3

An encapsulated product was prepared using the method of Example 1 but employing a starch solution containing 600 g of M200 maltodextrin, 120 g of CAPSUL modified starch, 6.0 g of ascorbic acid, 80 g of sucrose and 2,400 g of DI water, and an oil phase made from 60.0 g of lecithin and 1,194 g of omega-3 oil containing 2,000 ppm tocopherol. The total yield of product collected in bottles from the cyclone was 866 g. An additional 491 g of product was scraped from the dryer. The product had an SPME value of 15,744 after 48 hours at 50° C. (see Table 3), thus demonstrating improved oxidative stability over the Comparative Examples.

Example 4

An encapsulated product was prepared using the method of Example 1 but employing a starch solution containing 720 g of CAPSUL modified starch, 6.0 g of ascorbic acid, 80 g of sucrose and 2,400 g of DI water, and an oil phase made from 30.0 g of lecithin and 1,194 g of omega-3 oil containing 2,000 ppm tocopherol. The total yield of product collected in bottles from the cyclone was 1,131 g. An additional 459 g of product was scraped from the dryer. The product had an SPME value of 6,421 after 48 hours at 50° C. (see Table 3), thus demonstrating improved oxidative stability over the Comparative Examples.

Example 5

An encapsulated product was prepared using the method of Example 1 but employing a starch solution containing 600 g of M200 maltodextrin, 120 g of CAPSUL modified starch, 2.9 g of ascorbic acid, 5.8 g of citric acid, 80 g of trehalose (from Hayashibara Co.) and 1,200 g of DI water, and an oil phase made as follows. First, 288.8 g of omega-3 oil containing 2,000 ppm tocopherol and 28.9 g ARBORIS™ AS-2 phytosterol (from Arboris, LLC) were heated in a boiling waterbath while stirring. After the phytosterol had completely melted into the oil phase, an additional 288.8 g omega-3 oil containing 2,000 ppm tocopherol was added without any apparent change. The oil phase was poured into the starch solution and 28.9 g of lecithin was introduced into the oil phase. The oil phase was emulsified into the starch solution using a SILVERSON L2R high shear mixer and MICROFLUIDICS M110Y microfluidizer as in Example 1, then spray dried using a NIRO Mobile Minor lab dryer. The total yield of product collected in bottles from the cyclone was 508 g. An additional 522 g of product was scraped from the dryer. The product had an SPME value of 13,252 after 48 hours at 50° C. (see Table 3), thus demonstrating improved oxidative stability over the Comparative Examples.

Example 6

An encapsulated product was prepared using the method of Example 1 but employing an aqueous phase made by heating 1,200 g of DI water to 40° C. and adding 28.9 g of lecithin with stirring. After 15 minutes of stirring, 2.9 g of ascorbic acid and 5.8 g of citric acid were added. After another 30 minutes of stirring, 120 g of CAPSUL modified starch, 80 g of trehalose and 600 g of M200 maltodextrin were added. The resulting aqueous phase was held overnight under refrigeration. The following day, an oil phase made from 577.6 g of omega-3 oil containing 2,000 ppm tocopherol was poured into the aqueous phase and emulsified using a SILVERSON LT-1 high shear mixer (from Silverson Machines) operated at maximum speed for 15 minutes, thereby providing a coarse emulsion. An ice bath was used to cool the emulsion to approximately 30° C. before passing it through a MICROFLUIDICS M110Y microfluidizer operated at 110 MPa. The emulsion was spray dried using a NIRO Mobile Minor lab dryer operated using an inlet temperature of 225° C. and an outlet temperature of 90° C. The total yield of product collected in bottles from the cyclone was 607 g. An additional 473 g of product was scraped from the dryer. The product had an SPME value of 3,656 after 48 hours at 50° C. (see Table 3), thus demonstrating improved oxidative stability over the Comparative Examples.

Example 7

An encapsulated product was prepared using the method of Example 6 but employing an aqueous phase made by heating 1,200 g of DI water to 40° C. and adding 28.9 g of lecithin with stirring. After 20 minutes the temperature was increased to 80° C. and 600 g of M200 maltodextrin, 120 g of CAPSUL modified starch, 80 g of trehalose, 2.9 g of ascorbic acid and 5.8 g of citric acid were added with stirring. The resulting aqueous phase was cooled in an ice bath and refrigerated overnight. The following day, an oil phase made from 577.6 g of omega-3 oil containing 2,000 ppm tocopherol was poured into the aqueous phase and emulsified, microfluidized and spray dried as in Example 6. The total yield of product collected in bottles from the cyclone was 696 g. An additional 406 g of product was scraped from the dryer. The product had an SPME value of 8,141 after 48 hours at 50° C. (see Table 3), thus demonstrating improved oxidative stability over the Comparative Examples.

Example 8

An encapsulated product was prepared using the method of Example 6 but employing an aqueous phase made by heating 1,200 g of DI water to 40° C. and adding 28.9 g of lecithin with stirring. After 20 minutes the temperature was increased to 80° C. and 600 g of M200 maltodextrin, 120 g of CAPSUL modified starch, 80 g of trehalose, 2.9 g of ascorbic acid and 5.8 g of citric acid were added with stirring. The resulting aqueous phase was cooled in an ice bath and refrigerated overnight. The following day, an oil phase was made by heating 577.6 g of omega-3 oil containing 2,000 ppm tocopherol to 50° C., adding 17.3 g of ARBORIS AS-2 phytosterol and cooling to room temperature. The cooled oil phase was poured into the aqueous phase and emulsified and microfluidized as in Example 6. The emulsion was spray dried using a NIRO Mobile Minor lab dryer operated using an inlet temperature of 225° C. and an outlet temperature of 88° C. The total yield of product collected in bottles from the cyclone was 613 g. An additional 464 g of product was scraped from the dryer. The product had an SPME value of 4,773 after 48 hours at 50° C. (see Table 3), thus demonstrating improved oxidative stability over the Comparative Examples.

Example 9

An encapsulated product was prepared using the method of Example 6 but employing an aqueous phase made by heating 1,200 g of DI water to 40° C. and adding 40.0 g of lecithin with stirring. After 20 minutes the temperature was increased to 80° C. and 720 g of CAPSUL modified starch, 80 g of trehalose, 4.0 g of ascorbic acid and 8.0 g of citric acid were added with stirring. The resulting aqueous phase was cooled in an ice bath and refrigerated overnight. The following day, an oil phase was made by heating 796 g of omega-3 oil containing 2,000 ppm tocopherol to 50° C., adding 23.9 g of ARBORIS AS-2 phytosterol and cooling to room temperature. The cooled oil phase was poured into the aqueous phase and emulsified, microfluidized and spray dried as in Example 6. The total yield of product collected in bottles from the cyclone was 772 g. An additional 362 g of product was scraped from the dryer. The product had an SPME value of 2,582 after 48 hours at 50° C. (see Table 3), thus demonstrating improved oxidative stability over the Comparative Examples.

Example 10

An encapsulated product was prepared using the method of Example 6 but employing an aqueous phase made by first adding 1.20 g of MANUGEL™ DMB sodium alginate (from Nutrasweet Kelco) to 960 g of DI water, next adding 1.20 g of calcium chloride to 240 g of DI water, and combining the two solutions with stirring. The resulting mixture was heated to 40° C. followed by the addition of 40.0 g of lecithin with stirring. After 5 minutes the temperature was increased to 80° C. and 720 g of CAPSUL modified starch, 80 g of trehalose, 4.0 g of ascorbic acid and 8.0 g of citric acid were added with stirring. The resulting aqueous phase was cooled in an ice bath and refrigerated overnight. The following day, an oil phase was made by adding 23.9 g of ARBORIS AS-2 phytosterol to 796 g of omega-3 oil containing 2,000 ppm tocopherol and heating to 50° C. The warm oil phase was poured into the cooled aqueous phase and emulsified, microfluidized and spray dried as in Example 6. The total yield of product collected in bottles from the cyclone was 724 g. An additional 562 g of product was scraped from the dryer. The product had an SPME value of 4,619 after 48 hours at 50° C. (see Table 3), thus demonstrating improved oxidative stability over the Comparative Examples.

Example 11

Corn oil and corn oil bodies were extracted by adding 500 g of methylene chloride to 250 g of corn germ. The corn germ in methylene chloride was refrigerated and allowed to soak overnight in a sealed glass container before blending on low speed for 30 seconds using a WARING™ 2 quart lab blender (from Hamilton Beach Brands, Inc.). After soaking while refrigerated overnight, the blend was poured into a sheet of four layers of cheesecloth and squeezed in order to remove most of the liquid. The permeate was placed in a shallow glass pan and the methylene chloride was allowed to evaporate in a fume hood for over 24 hours. The resulting oil-solids mixture weighed 40 g and had an apparent corn-like odor. The solids contained phospholipids and the proteins associated with oil bodies in addition to other solids.

An aqueous phase was prepared by first adding 1.20 g of sodium alginate to 1184 g of DI water, next adding 1.20 g of calcium chloride to 296 g of DI water, combining the two solutions with stirring, and then adding lecithin, CAPSUL modified starch, trehalose, ascorbic acid and citric acid using the amounts and procedures employed in Example 10. The resulting aqueous phase was cooled in an ice bath and refrigerated overnight, followed by addition of 40 g of the oil-solids mixture. An oil phase was prepared by adding 23.9 g of ARBORIS AS-2 phytosterol to 756 g of omega-3 oil containing 2,000 ppm tocopherol and heating to 50° C. The warm oil phase was poured into the cooled aqueous phase and emulsified, microfluidized and spray dried as in Example 6. The total yield of product collected in bottles from the cyclone was 588 g. An additional 398 g of product was scraped from the dryer. The product had an SPME value of 3,345 after 48 hours at 50° C. (see Table 3), thus demonstrating improved oxidative stability over the Comparative Examples.

Example 12

An encapsulated product was prepared using the method of Example 6 but employing 103 g (rather than 40 g) of the oil-solids mixture in the aqueous phase. The total yield of product collected in bottles from the cyclone was 791 g. An additional 488 g of product was scraped from the dryer. The product had an SPME value of 3,562 after 48 hours at 50° C. (see Table 3), thus demonstrating improved oxidative stability over the Comparative Examples.

Example 13

A 450 g portion of dry calcium chloride was added to 1350 g of ROUNDY'S™ canola oil (from Creative Products, Inc. of Rossville) and lightly ground using a Silverson LT-1 high shear mixer operated at maximum speed for 20 minutes. The resulting calcium chloride dispersion was transferred to a BUHLER™ PML2 laboratory media mill (from Buhler Technology Group) and kept gently suspended, then bead milled for 150 minutes using 0.4 mm YTZ (yttria-stabilized zirconia) media, a rotor speed of 3,500 rpm and a 40% recirculating pump rate. This reduced the size of the calcium chloride to about 1.16 and provided a 25 wt. % calcium chloride suspension in canola oil. The aqueous phase was made by heating 1,480 g of DI water to 40° C. and adding 40.0 g of lecithin with stirring. After 20 minutes the temperature was increased to 80° C. and 720 g of CAPSUL modified starch, 80 g of trehalose, 4.0 g of ascorbic acid, 8.0 g of citric acid and 1.2 g of sodium alginate were added with stirring. The resulting aqueous phase was held overnight under refrigeration. The following day, an oil phase was made by adding 2.0 g of the 25 wt. % calcium chloride dispersion in canola oil to 796 g of omega-3 oil containing 2,000 ppm tocopherol, heating to 50° C., adding 23.9 g of ARBORIS AS-2 phytosterol and cooling to room temperature. The cooled oil phase was poured into the aqueous phase and emulsified using a SILVERSON LT-1 high shear mixer operated at maximum speed for 15 minutes, thereby providing a coarse emulsion. An ice bath was used to cool the emulsion to approximately 30° C. before passing it through a MICROFLUIDICS M110Y microfluidizer operated at 138 MPa. The emulsion was spray dried using a NIRO Mobile Minor lab dryer operated using an inlet temperature of 225° C. and an outlet temperature of 90° C. The total yield of product collected in bottles from the cyclone was 878 g. An additional 293 g of product was scraped from the dryer. The product had an SPME value of 3,456 after 48 hours at 50° C. (see Table 3), thus demonstrating improved oxidative stability over the Comparative Examples.

Example 14

A 2.0 g portion of 75 bloom gelatin was added to 1480 g of 80° C. DI water and allowed to hydrate fully. An ice bath was used to cool the gelatin solution to 40° C. and then 40.0 g of lecithin was added with stirring. After twenty minutes the temperature was increased to 80° C. and then 720 g of CAPSUL modified starch, 80 g of trehalose, 4.0 g of ascorbic acid, 8.0 g of citric acid and 1.2 g of sodium alginate were added with stirring. The resulting aqueous phase was held overnight under refrigeration. The following day, an oil phase was made by adding 2.0 g of the 25 wt. % calcium chloride dispersion in canola oil from Example 13 to 796 g of omega-3 oil containing 2,000 ppm tocopherol, heating to 60° C. and adding 23.9 g of ARBORIS AS-2 phytosterol. The warm oil phase and cool aqueous phase were mixed using a SILVERSON LT-1 high shear mixer operated at maximum speed for 15 minutes, thereby providing an emulsion. An ice bath was used to cool the emulsion to approximately 30° C. The emulsion was spray dried using a NIRO Mobile Minor lab dryer operated using an inlet temperature of 225° C. and an outlet temperature of 90° C. The total yield of product collected in bottles from the cyclone was 960 g. An additional 377 g of product was scraped from the dryer. The product had an SPME value of 4,746 after 48 hours at 50° C. (see Table 3), thus demonstrating improved oxidative stability over the Comparative Examples.

Example 15

Corn oil and corn oil bodies were extracted from dried corn germ. First, 262.7 g of dried, cold corn germ were removed from a −28° C. freezer, placed in a WARING 2 quart lab blender and ground on the low setting for 1.25 minutes, with a halt each 15 seconds to scrape down the sides. The ground corn germ was then placed in a 0.95 L bottle to which 500 g of water was added. The bottle was placed on a lab shaker for 60 minutes on low speed, stored at room temperature overnight, returned to the lab shaker for 5 hours on low speed and then stored in a refrigerator for 4 days. The mixture was centrifuged in 45 ml portions at 6000 rpm for 30 minutes. All of the liquid and floating material from the centrifuge tubes was collected and combined and then 15 ml of water was added to the tubes to float any remaining oil containing material. A total of 448 g of corn homogenate was collected. Next, 27 g of $CaCl_2$ was dissolved in 50 g of water and cooled to room temperature. The Ca solution was added to the bottle of corn homogenate. The bottle was placed on a lab shaker for 1 hour on low speed. The bottle contents were transferred to a separatory funnel and stored in a refrigerator overnight. The funnel contents separated and the $CaCl_2$/water layer was removed. A 519 g portion of water was added to the separatory funnel and the separatory funnel was shaken gently and returned to the refrigerator for 2 hours. The water layer was removed by separation and the water washing and separation steps were repeated 3 more times. A corn oil body layer weighing 133.7 g was collected.

A 450 g portion of dry calcium chloride was added to 1350 g of ROUNDY'S™ canola oil and lightly ground using a Silverson LT-1 high shear mixer operated at maximum speed for 20 minutes. The resulting calcium chloride dispersion was transferred to a BUHLER PML2 laboratory media mill and kept gently suspended, then bead milled for 150 minutes using 0.4 mm YTZ (yttria-stabilized zirconia) media, a rotor speed of 3,500 rpm and a 40% recirculating pump rate. This reduced the size of the calcium chloride particles to about 1.16 μm and provided a 25 wt. % calcium chloride suspension in canola oil. The aqueous phase was made by heating 1480 g of DI water to 40° C. and then adding 40.0 g of ULTRALEC F lecithin with stirring. After twenty minutes of stirring the temperature was increased to 80° C. and then 720 g of CAPSUL modified starch, 80 g of trehalose, 4.0 g of ascorbic acid, 8.0 g of citric acid, 1.2 g MANUGEL™ LBA sodium alginate (from Nutrasweet Kelco), and 15.0 g oat fiber were added. The solution was cooled via an ice bath before refrigerating overnight. The following day, 133.7 g of the corn oil bodies were added directly to the aqueous phase. For the oil phase, 2.0 g of the 25 wt. % suspension of calcium chloride in canola oil was added to 662.3 g of omega-3 oil containing 2,000 ppm tocopherol and heated to 50° C., followed by the dissolution of 23.9 ARBORIS AS-2 phytosterol in the 50° C. oil phase and cooling to room temperature. The cooled oil phase was poured into the aqueous phase and emulsified and spray dried as in Example 13 but without use of the microfluidizer. The total yield of product collected in bottles from the cyclone was 983 g. An additional 371 g of product was scraped from the dryer. The product had an SPME value of 2,720 after 48 hours at 50° C. (see Table 3), thus demonstrating improved oxidative stability over the Comparative Examples.

Example 16

To a 98.00 g portion of the spray dried encapsulated powder from Example 15 was added 2.00 g of SYLOPOL™ 952 precipitated silica gel (from Grace Davison) in a 0.95 L bottle and then shaken by hand for about 10 minutes to obtain a uniform mixture. The product had an SPME value of 2,047 after 48 hours at 50° C. (see Table 3), thus demonstrating improved oxidative stability over the Comparative Examples.

Example 17

To a 95.00 g portion of the spray dried encapsulated powder from Example 5 was added 5.00 g of finely ground oat fiber in a 0.95 L bottle and then shaken by hand for about 10 minutes to obtain a uniform mixture. The product had an SPME value of 2,651 after 48 hours at 50° C. (see Table 3), thus demonstrating improved oxidative stability over the Comparative Examples.

The 48 Hour SPME results mentioned above are shown below in Table 3, along with the calculated oil load, initial SPME value, ratio of the 48 hour SPME value to initial SPME value, and a subjective evaluation of the initial odor for the unencapsulated oil or dry powder. The encapsulated materials in Examples 1 and 2 exhibited significantly improved oxidative stability over the Comparative Examples. It should be noted that the detection of an odor does not mean that the tested material would be unsuitable in a food product, since in many cases the slight odor detected would be masked by other food product ingredients.

TABLE 3

| Example No. | Oil Load | Initial SPME | 48 Hr. SPME | Ratio 48 Hr./Initial SPME | Initial Odor |
|---|---|---|---|---|---|
| Comp. Ex. 1 | 100 | 1565 | 29000 | 18.53 | Slight fish |
| Comp. Ex. 2 | 100 | 456 | 19085 | 41.85 | Very slight fish |
| Comp. Ex. 3 | 100 | 3506 | 37904 | 10.81 | Slight fish |
| Comp. Ex. 4 | 20 | 1952 | 36544 | 18.72 | Slight fresh fish |
| Comp. Ex. 5 | 20 | 2796 | 39985 | 14.30 | Slight fresh fish |
| Comp. Ex. 6 | 20 | 1424 | 38840 | 27.28 | Slight fresh fish |
| Example 1 | 40 | 10939 | 19796 | 1.81 | Low odor, very slight fish/lecithin |
| Example 2 | 50 | 4970 | 10355 | 2.08 | Low odor, very slight fish/lecithin |
| Example 3 | 60 | 989 | 15744 | 15.92 | Slight fish |
| Example 4 | 60 | 1743 | 6421 | 3.68 | Mild fish |
| Example 5 | 40 | 3000 | 13252 | 4.42 | Low fish |
| Example 6 | 40 | 2775 | 3656 | 1.32 | Slight rancid fish, slight burnt/caramelized notes |
| Example 7 | 40 | 4808 | 8141 | 1.69 | Sight rancid fish (less than Example 6), slight sweet/dairy notes |
| Example 8 | 40 | 5068 | 4773 | 0.94 | Slight dairy note |
| Example 9 | 50 | 4277 | 2582 | 0.60 | Slight burnt note |
| Example 10 | 50 | 4026 | 4619 | 1.15 | Slight burnt sugar note |
| Example 11 | 50 | 2975 | 3345 | 1.12 | Slight burnt sugar note, slight fish, plant extract/leafy odor |
| Example 12 | 50 | 3443 | 3562 | 1.03 | Low odor, leafy odor |
| Example 13 | 50 | 5805 | 3456 | 0.60 | Very low odor |
| Example 14 | 50 | 5440 | 4746 | 0.87 | Slight burnt notes, leafy note |
| Example 15 | 50 | 5010 | 2720 | 0.54 | Slight burnt, leafy, very slight fish |
| Example 16 | 50 | 1220 | 2047 | 1.68 | very low overall odor, slight dairy |
| Example 17 | 50 | 5946 | 2651 | 0.45 | Slight burnt, leafy, very slight fish |

Comparative Example 7

A 2.1 g portion of MEG-3™ omega-3 fish oil coated with fish gelatin (from Ocean Nutrition) was mixed with 11 g of TANG™ drink mix powder (from Kraft Foods, Inc.) and then added to 237 cm$^3$ of water. The coated omega-3 oil did not disperse to form a uniform drink. Instead, the coated omega-3 oil formed clumps which settled to the bottom of the drink.

Examples 18 through 21

A 2.51 g portion of the spray dried encapsulated material from Example 11 was mixed with 11 g of TANG powder and then added to 237 cm$^3$ of water. The encapsulated material and TANG powder dispersed to form a uniform drink (Example 18). Similar results were obtained when the spray dried encapsulated materials from Example 9, 10 or 15 were mixed with TANG powder and added to water. In each instance, the encapsulated material and TANG powder dispersed to form a uniform drink (Examples 19, 20 and 21).

Examples 22 through 24

A 0.85 g portion of the spray dried encapsulated material from Example 11 was mixed into a 1.9 L container of TROPICANA™ Pure Premium orange juice (from Tropicana Manufacturing Company, Inc.). The encapsulated material dispersed in the orange juice to form a uniform drink (Example 22). Similar results were obtained when the spray dried encapsulated materials from Examples 9 or 10 were mixed with the orange juice. In each instance, the encapsulated material dispersed in the orange juice to form a uniform drink (Examples 23 and 24).

Examples 25 through 28

A 2.51 g portion of the spray dried encapsulated material from Example 11 was mixed with 454 g of BETTY CROCKER® Pound Cake Mix (from General Mills Sales, Inc.) followed by the addition of 177 ml of water and 2 eggs. The ingredients were mixed at low speed using a KITCHENAID™ mixer (from KitchenAid, U.S.A.) for 30 seconds, followed by mixing at medium speed for 3 minutes. The mixture was poured into a 23 cm×13 cm loaf pan, placed in a preheated 177° C. oven and baked for 50 minutes until a toothpick inserted in the center of cake came out clean. The cake was cooled for 10 minutes in the pan, then removed and cooled to room temperature on a wire rack. The encapsulated material appeared to be well dispersed in the pound cake and baked without any apparent fishy smell during baking. There was no fishy smell or taste in the finished pound cake (Example 25). Similar results were obtained when 4.01 g portions of the spray dried encapsulated materials from Examples 9, 10 or 15 were mixed with 454 g of Pound Cake Mix, 177 ml of water and 2 eggs and baked as described above. The encapsulated materials appeared to be well dispersed in the pound cake and baked without any apparent fishy smell during baking. There was no fishy smell or taste in the finished pound cakes (Examples 26, 27 and 28).

Preparations 1 and 2

Oil Cores

A nitrogen blanket over freshly distilled oil can result in appreciable oxidation of the oil if even as little as 1% oxygen is present in the nitrogen blanket. All handling of oil to be encapsulated desirably would be done using purified nitrogen. Also, to insure metallic prooxidants would be minimized, glass lined vessels may be used after distillation. Oil Cores may be made by a number of methods including emulsification and organogel particle formation. One such example could employ 500 grams of refined fish oil mixed with 5 grams of ground calcium carbonate (particle size less than 5 micrometers), 50 grams of phytosterols such as a mixture of campesterol and sitosterol, and at least one antioxidant such as 0.5 g of α-tocopherol. The mixture may be heated in the absence of oxygen to melt and dissolve the phytosterols (140-170° C.) and the resulting solution may be atomized in a cold chamber to produce solid particles of the mixture (Preparation 1).

Oil cores or droplets may also be made by emulsification methods wherein the same components as described in Preparation 2 would be mixed and added to 1000 grams of water. The two non-miscible liquids may be vigorously mixed with ultrasonic mixers, high pressure homogenizers, or high speed mixers. The resultant mixtures would include a plurality of oil droplets or cores. One such example could employ 500 grams of refined fish oil mixed with 5 grams of ground calcium carbonate (particle size less than 5 micrometers), 50 grams of phytosterol such as a mixture of campesterol and sitosterol, and at least one antioxidant such as 0.5 g of α-tocopherol. This oil phase would be mixed into 1000 grams of water in a nitrogen-purged vessel equipped with a high shear Cowles mixing blade. The mixer would be turned on to its maximum rpm setting to produce oil droplets or cores suspended in a continuous water matrix (Preparation 2).

Preparation 3

Phospholipid Shell Formation

Oil cores may also be prepared in situ with formation of a phospholipid shell structure. One such example for direct preparation of the phospholipid shell could employ a 33 L suspension containing 0.25 M sucrose, 50 mM Bis-Tris, pH7.2, and a refined fish oil dispersion containing 500 g fish oil, 5 grams of ground calcium carbonate (particle size less than 5 micrometers), 50 grams of phytosterol such as a mixture of campesterol and sitosterol, and at least one antioxidant such as 0.5 g of α-tocopherol, and phospholipid (PL) (4.5 g) in a 50 L nitrogen purged vessel. The mixture could be mixed with a high speed Cowles dissolver (Preparation 3).

Preparation 4

Hydrocolloid Layer

The hydrocolloid layer may include a variety of crosslinkable solidifiable hydrocolloids such as alginates, pectates, carageenates, pectin, gelatin/acacia, and others. This layer will provide an added layer of stability for the phospholipid, the ability to add fiber for a hard shell coating and oxidation protection, and the ability to add water-soluble antioxidants to help protect the oxidatively unstable oil core. One such example could be made by slowly adding to the mixture prepared in Preparation 3, with stirring, 5 L of 5 wt % sodium alginate aqueous solution. The alginate solution may contain phytosterol and may contain other additives such as insoluble cellulosic fiber, soluble fiber such as inulin, or antioxidants. For example, in addition to the sodium alginate, the alginate solution may contain 5 grams of phytosterol such as a mixture of campesterol and sitosterol, 100 grams of dispersed ethyl cellulose and 5 grams of anthocyanin antioxidant. The mixture may be allowed to stir for 3 hours to complete the reaction of the calcium ions from the dispersed calcium carbonate in the oil phase with the alginate in solution to form an alginate/fiber/antioxidant layer (Preparation 4).

Preparations 5 through 8

Fiber/Carbohydrate/Protein Layer

To form a stable, dry powder the materials from Preparations 3 or 4 may be spray dried as follows: The solutions described above may be fed to a Niro Lab Dryer at 10 mL/min with the inlet temperature of the dryer set at 120° C. The phospholipid shell structure may be dried to a particle size of 5-100 micrometers with a moisture content of 3-8 wt % (Preparations 5 and 6). Alternatively, to the solutions described in Preparations 3 or 4 an aqueous solution may be added containing 50 grams of sodium caseinate, 50 grams of trehalose, 50 grams of citrus fiber (from Fiberstar), 5 grams of phytosterol such as a mixture of campesterol and sitosterol and 500 g water, and fed to a Niro Mobile Minor lab dryer as in Example 1. The resulting encapsulated structure may be dried to a particle size of 5-100 micrometers with a moisture content of 3-8 wt % (Preparations 7 and 8).

Preparations 9 through 12

Fat (Lipid) Layer

The Preparation 5 through 8 dry powders may be added to melted waxes, phytosterols or mixtures of both and prilled as described in U.S. Pat. No. 7,237,679 B1 to form fat or lipid encapsulated particles. One such example could employ 500 grams of the Preparation 5 powder in 700 grams of molten DRITEX™ C-41V hydrogenated vegetable oil (from ACH Food & Nutrition) at 75° C. and 50 grams of phytosterol such as a mixture of campesterol and sitosterol. The molten melt would be prilled or atomized to form particles with a particle size of 300-600 micrometers.

Although specific examples, compositions, ingredients, temperatures and proportions have been disclosed in various aspects of the present invention, those disclosures are intended to be exemplary of species within a generic invention.

We claim:

1. An encapsulated material comprising an oxidation-sensitive core covered by at least one shell comprising a dried phospholipid layer, starch and at least one further carbohydrate, and having at least one phytosterol in the core or in a shell surrounding the core.

2. The encapsulated material of claim 1 wherein the core is a liquid at room temperature.

3. The encapsulated material of claim 1 wherein the core comprises a phytosterol, antioxidant, polyunsaturated fatty acid or triacylglycerol.

4. The encapsulated material of claim 1 wherein the core comprises an omega-3 or omega-6 polyunsaturated fatty acid.

5. The encapsulated material of claim 1 wherein the core comprises an acidulant, animal product, carotenoid, catalyst, drug, dye, enzyme, flavor, fragrance, lutein, lycopene, metal complex, natural color, nutraceutical, pigment, polyphenolic, processed plant material, metabiotic, probiotic, protein, squalene, tocopherol, tocotrienol, vitamin, unsaturated organic compound, or mixture thereof.

6. The encapsulated material of claim 1 wherein the core is greater than 30 wt. % of the encapsulated material.

7. The encapsulated material of claim 1 wherein the phospholipid layer contains 8 wt. % or less of available water.

8. The encapsulated material of claim 1 wherein the phospholipid layer comprises lecithin or chemically modified lecithin.

9. The encapsulated material of claim 1 wherein the phospholipid layer comprises phytosterol.

10. The encapsulated material of claim 1 wherein the phospholipid layer comprises natural or chemically modified phospholipid, phytosterol and natural or chemically modified starch.

11. The encapsulated material of claim 1 wherein the further carbohydrate comprises natural or chemically modified maltodextrin, natural or chemically modified sucrose, or natural or chemically modified trehalose.

12. The encapsulated material of claim 1 comprising a layer containing natural or chemically modified carbohydrate, natural or chemically modified starch, natural or chemically modified alginate, insoluble fiber, soluble fiber, protein or a lipid.

13. The encapsulated material of claim 12 wherein the protein comprises gelatin.

14. The encapsulated material of claim 1 comprising a hydrocolloid-containing layer which is crosslinked by a calcium salt source in the core or in an adjacent layer.

15. The encapsulated material of claim 1 having a solid phase micro extraction value after 48 hours at 50° C. that is less than 8,000, and a ratio of solid phase micro extraction value after 48 hours at 50° C. to initial solid phase micro extraction value that is less than 8.

16. A food product comprising the encapsulated material of claim 1.

17. The food product of claim 16 wherein the food is a baked food product, dry juice drink or liquid juice drink.

* * * * *